United States Patent
Ota

(10) Patent No.: US 11,194,061 B2
(45) Date of Patent: Dec. 7, 2021

(54) OPTICAL DETECTOR AND OPTICAL DETECTION DEVICE

(71) Applicant: HAMAMATSU PHOTONICS K.K., Hamamatsu (JP)

(72) Inventor: Ryosuke Ota, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

(21) Appl. No.: 16/623,032

(22) PCT Filed: Jun. 19, 2018

(86) PCT No.: PCT/JP2018/023272
§ 371 (c)(1),
(2) Date: Dec. 16, 2019

(87) PCT Pub. No.: WO2018/235810
PCT Pub. Date: Dec. 27, 2018

(65) Prior Publication Data
US 2021/0116586 A1   Apr. 22, 2021

(30) Foreign Application Priority Data
Jun. 23, 2017 (JP) .............. JP2017-123011

(51) Int. Cl.
*G01T 1/20* (2006.01)
*A61B 6/03* (2006.01)
(Continued)

(52) U.S. Cl.
CPC ............ *G01T 1/2018* (2013.01); *A61B 6/037* (2013.01); *G01T 1/208* (2013.01); *H01L 27/14663* (2013.01)

(58) Field of Classification Search
CPC . G01T 1/2018; G01T 1/208; H01L 27/14663; A61B 6/037
See application file for complete search history.

(56) References Cited

U.S. PATENT DOCUMENTS

| | | | |
|---|---|---|---|
| 2001/0020863 A1* | 9/2001 | Cova | G01J 1/44 327/514 |
| 2009/0121142 A1* | 5/2009 | Heismann | G01T 1/2018 250/363.04 |

(Continued)

FOREIGN PATENT DOCUMENTS

| JP | S58-30628 A | 2/1983 |
|---|---|---|
| JP | 2010-169516 A | 8/2010 |

(Continued)

OTHER PUBLICATIONS

Alexander M Grant et al., "A new dual threshold time-over-threshold circuit for fast timing in PET", Bristol GB, Jun. 3, 2014 vol. 59,No. 13, p. 3421-p. 3430.

(Continued)

*Primary Examiner* — Kiho Kim
(74) *Attorney, Agent, or Firm* — Faegre Drinker Biddle & Reath LLP

(57) ABSTRACT

A photodetector includes N photodetection pixels arranged one-dimensionally or two-dimensionally and each for generating a detection signal in response to incidence of light, and a single output terminal for outputting the detection signal generated in each of the N photodetection pixels. Each of the N photodetection pixels includes an avalanche photodiode operating in Geiger mode, and a quenching resistor connected in series to the avalanche photodiode, and the N photodetection pixels are configured to output detection signals having time waveforms different from each other.

6 Claims, 12 Drawing Sheets

(51) Int. Cl.
    *G01T 1/208*     (2006.01)
    *H01L 27/146*     (2006.01)

(56) References Cited

U.S. PATENT DOCUMENTS

| | | | |
|---|---|---|---|
| 2011/0108702 A1* | 5/2011 | Jackson | H01L 27/1446 250/207 |
| 2014/0209804 A1 | 7/2014 | Lee et al. | |

FOREIGN PATENT DOCUMENTS

| | | |
|---|---|---|
| JP | 2012-60012 A | 3/2012 |
| JP | 2014-090034 A | 5/2014 |
| JP | 5531021 B2 | 6/2014 |
| JP | 2014-160042 A | 9/2014 |
| JP | 2014-215142 A | 11/2014 |
| JP | 2014-241543 A | 12/2014 |
| JP | 2016-16130 A | 2/2016 |
| JP | 2017-101998 A | 6/2017 |
| JP | 2017-117836 A | 6/2017 |
| WO | WO-2007/043137 A1 | 4/2007 |
| WO | WO-2015/128905 A1 | 9/2015 |
| WO | WO-2017/038133 A1 | 3/2017 |

OTHER PUBLICATIONS

Chang, Chen-Ming et al., "Time-over-threshold for pulse shape discrimination in a time-of-flight phoswich PET detector," Phys. Med. Biol., 2017, vol. 62, pp. 258-271.
International Preliminary Report on Patentability dated Jan. 2, 2020 for PCT/JP2018/023272.

* cited by examiner

*Fig.12*

| SCINTILLATOR | RISE TIME $\tau r$(ns) | FALL TIME $\tau d$(ns) |
|---|---|---|
| LSO:Ce | 0.079 | 39.6 |
| LYSO:Ce | 0.089 | 43 |
| LaBr3:Ce | 0.28 | 15.4 |
| GSO:Ce | 6 | 65 |
| GAGG:Ce | 4.6 | 95 |

OPTICAL DETECTOR AND OPTICAL DETECTION DEVICE

TECHNICAL FIELD

The present invention relates to a photodetector and a photodetection device used for detecting light.

BACKGROUND ART

In a positron emission tomography (PET) apparatus, a substance labeled with a radioisotope (RI) that emits positrons is applied to a subject as a tracer. Then, a radiation detector measures a pair of γ-rays generated by annihilation of the positron emitted from the RI substance and the electron in the normal substance, thereby obtaining information about the subject.

In a measurement apparatus, such as the PET apparatus, a radiation detector used for detecting radiation rays, such as γ-rays, is appropriately configured by combining, for example, a scintillator that generates scintillation light in response to incidence of a radiation ray and a photodetector that detects the scintillation light and outputs a detection signal (see, for example, Patent Document 1).

CITATION LIST

Patent Literature

Patent Document 1: Japanese Patent Application Laid-Open Publication No. 2014-160042
Patent Document 2: Japanese Patent Publication No. 5531021

Non Patent Literature

Non Patent Document 1: Chen-Ming Chang et al., "Time-over-threshold for pulse shape discrimination in a time-of-flight phoswich PET detector", Phys. Med. Biol. Vol. 62 (2017) pp. 258-271

SUMMARY OF INVENTION

Technical Problem

As a photodetector in a radiation detector of a PET apparatus, for example, a multi-pixel photon counter (MPPC) is used. The MPPC is one of silicon photomultipliers (SiPM), and includes a plurality of photodetection pixels (micropixels) that each generate a detection signal in response to incidence of light, and a single output terminal that outputs the detection signal generated in each of the photodetection pixels to the outside. Further, the MPPC is also widely used in fields other than the field of a PET apparatus.

The MPPC is capable of detecting a single photon incident on a photodetection pixel, and can be appropriately applied to photon counting or the like in weak light measurement. However, the MPPC has a plurality of photodetection pixels, but has one output terminal that outputs a detection signal to the outside, and cannot determine which pixel has detected light.

The present invention has been made to solve the above problem, and an object thereof is to provide a photodetector and a photodetection device that are capable of appropriately determining, in a configuration having a plurality of photo-detection pixels and a single output terminal, which photodetection pixel has detected light.

Solution to Problem

A photodetector according to the present invention includes (1) N photodetection pixels (N is an integer of 2 or more) arranged one-dimensionally or two-dimensionally and each for generating a detection signal in response to incidence of light, and (2) a single output terminal for outputting the detection signal generated in each of the N photodetection pixels, and (3) each of the N photodetection pixels includes an avalanche photodiode operating in Geiger mode, and a quenching resistor connected in series to the avalanche photodiode, and (4) the N photodetection pixels are configured to output detection signals having time waveforms different from each other.

In the above photodetector, the single output terminal is provided for the detection signals generated in the N photodetection pixels, and each photodetection pixel is configured to include the avalanche photodiode operating in Geiger mode, and the quenching resistor. Further, in this configuration, the N photodetection pixels used for detecting incident light are configured to output detection signals having time waveforms different from each other. With this configuration, it is possible to appropriately identify and determine the photodetection pixel detecting incident light based on the time waveform of the detection signal, for example, a time constant indicating the time waveform of the detection signal.

A photodetection device according to the present invention includes (1) a photodetector having the above configuration, (2) a time waveform measurement unit for measuring the time waveform of the detection signal output from the output terminal of the photodetector, and (3) an analysis unit for obtaining a time constant indicating the time waveform of the detection signal based on a measurement result by the time waveform measurement unit.

In the above photodetection device, the photodetector including the N photodetection pixels configured to output detection signals having time waveforms different from each other and the single output terminal that outputs the detection signal is used, and the time waveform measurement unit and the analysis unit are provided for the detection signal output from the photodetector. With this configuration, the analysis unit obtains the time constant indicating the time waveform of the detection signal, and it is thereby possible to appropriately acquire information that the detection signal is output from which one of the N photodetection pixels.

Advantageous Effects of Invention

According to a photodetector and a photodetection device of the present invention, a single output terminal is provided for detection signals generated in N photodetection pixels, each photodetection pixel is constituted by an avalanche photodiode operating in Geiger mode and a quenching resistor, and the N photodetection pixels are configured to output detection signals having time waveforms different from each other, and it is thereby possible to appropriately determine a photodetection pixel detecting light.

BRIEF DESCRIPTION OF DRAWINGS

FIG. 12 is a table showing rise times and fall times of time waveforms of scintillation light output from scintillators.

DESCRIPTION OF EMBODIMENTS

Figure 1:
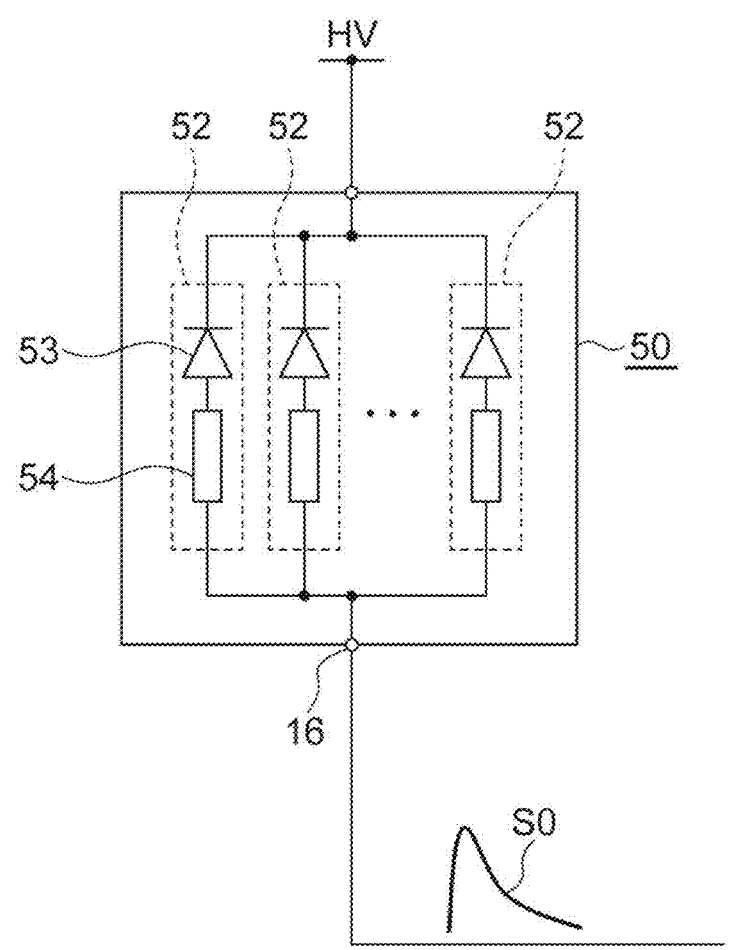
FIG. 1 is a diagram schematically illustrating a configuration of a photodetector of a first embodiment.

Hereinafter, embodiments of a photodetector and a photodetection device according to the present invention will be described in detail with reference to the drawings. In the description of the drawings, the same elements will be denoted by the same reference signs, without redundant description. Further, the dimensional ratios in the drawings are not always coincident with those in the description.

Figure 2:
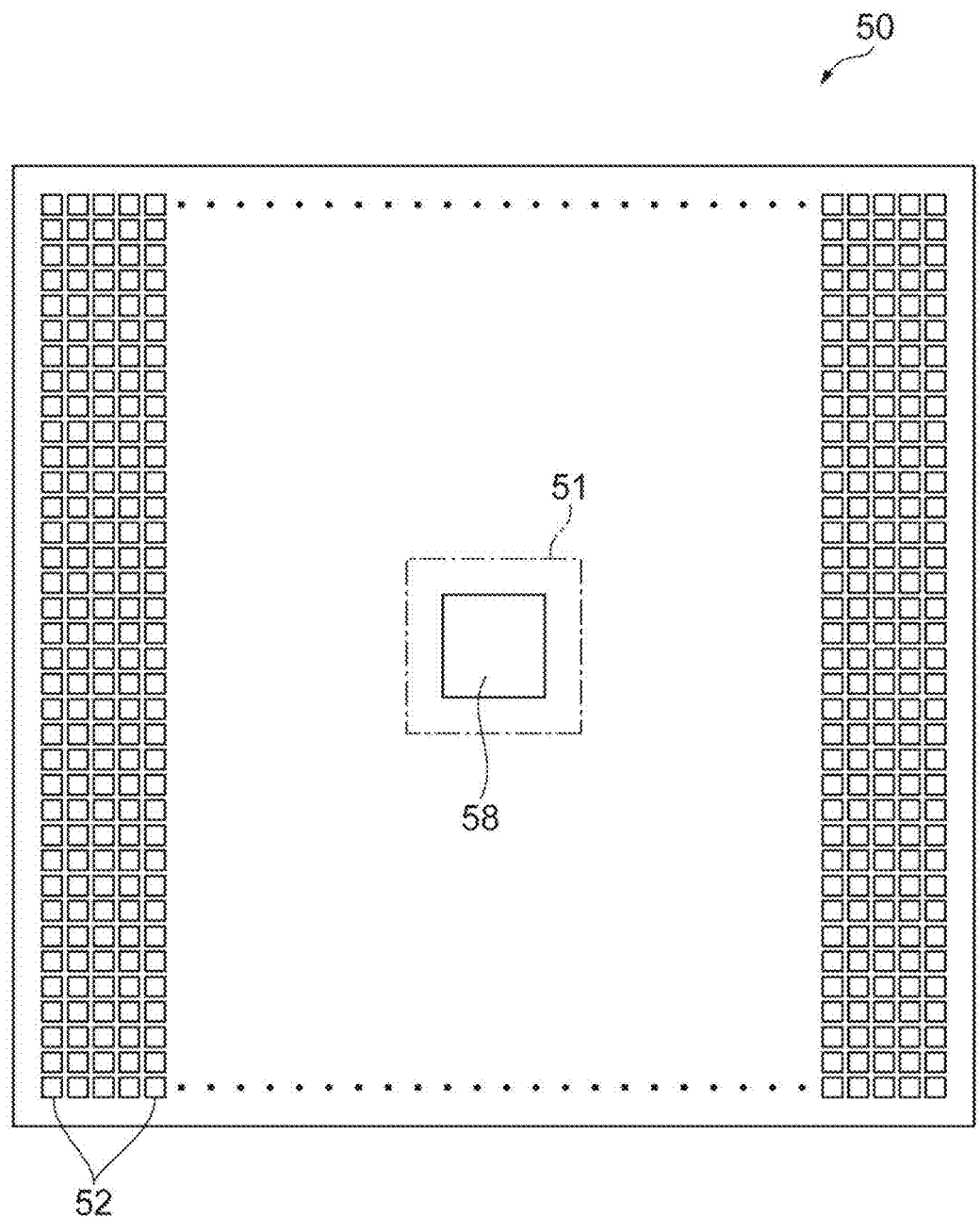
FIG. 2 is a plan view illustrating the configuration of the photodetector illustrated in FIG. 1.
Figure 3:
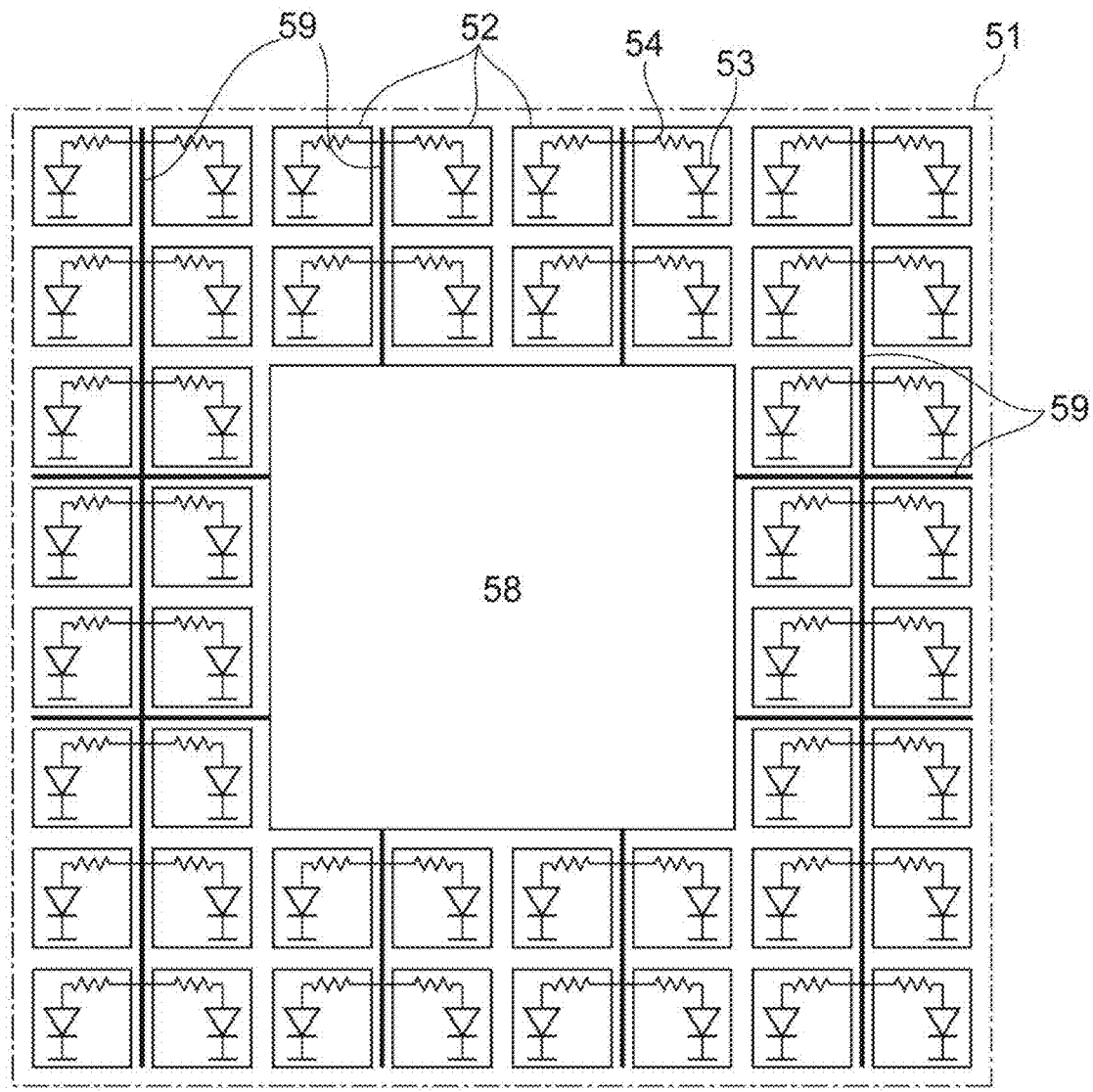
FIG. 3 is a plan view illustrating the configuration of the partially enlarged photodetector illustrated in FIG. 2.

FIG. 1 is a diagram schematically illustrating a configuration of a photodetector of a first embodiment. A photodetector 50 according to the present embodiment is configured, with N being an integer of 2 or more, as an MPPC including N photodetection pixels (photodetection units) 52. FIG. 2 is a plan view illustrating a configuration of the photodetector 50 illustrated in FIG. 1. Further, FIG. 3 is a plan view illustrating the configuration of the partially enlarged photodetector 50 illustrated in FIG. 2. FIG. 3 is an enlarged view of a central region 51 of the photodetector 50 illustrated in FIG. 2. In addition, regarding a specific configuration of the MPPC, Patent Document 1 can be referred to, for example.

The photodetector 50 includes N photodetection pixels (micropixels) 52 that are arranged one-dimensionally or two-dimensionally and each generate a detection signal S0 in response to incidence of light, and a single output terminal 16 that outputs the detection signal S0 generated in each of the N photodetection pixels 52 to the outside.

In the configuration example illustrated in FIG. 2 and FIG. 3, the N photodetection pixels 52 are two-dimensionally arranged on the detector chip of the photodetector 50. Further, at the center of the detector chip, a common electrode 58 for collecting the detection signals S0 from the photodetection pixels 52 is disposed. In addition, in FIG. 2, the photodetection pixels 52 are illustrated only in the vicinity of both ends of the detector chip in order for the common electrode 58 to be easily recognized and the like.

Each of the N photodetection pixels 52 of the photodetector 50 includes an avalanche photodiode (APD) 53 that operates in Geiger mode, and a quenching resistor 54 connected in series to the APD 53. Further, the quenching resistor 54 is connected to the common electrode 58 and the output terminal 16 via a signal line 59 as illustrated in FIG. 3. The detection signal S0 generated in each photodetection pixel 52 is output from the output terminal 16 to the outside via the signal line 59 and the common electrode 58.

Further, the N photodetection pixels 52 of the photodetector 50 are configured to output detection signals S0 having time waveforms different from each other (time constants different from each other). Specifically, in the present configuration example, the photodetector 50 is configured such that the quenching resistors 54 that determine, in the N photodetection pixels 52, the time waveforms and time constants of the detection signals have resistance values different from each other.

The effect of the photodetector 50 according to the above embodiment is described.

In the photodetector 50 illustrated in FIG. 1 to FIG. 3, the single output terminal 16 is provided for the detection signals S0 generated in the N photodetection pixels 52, and each photodetection pixel 52 includes the APD 53 operating in Geiger mode, and the quenching resistor 54. Further, in this configuration, the N photodetection pixels 52 used for detecting light are configured to output detection signals S0 having time waveforms different from each other.

With this configuration, it is possible to appropriately identify and determine the photodetection pixel 52 detecting incident light based on the time waveform of the detection signal S0, for example, a time constant τ that is a parameter indicating the time waveform of the detection signal S0. With the above configuration, for example, it is possible to obtain information on the incident position of light in weak light measurement in which a single photon is incident on and detected by the photodetector 50, and to improve the spatial resolution in photodetection.

Further, with the configuration in which the photodetection pixel 52 includes the APD 53 and the quenching resistor 54 as described above, the time waveform of the detection signal S0 generated in the photodetection pixel 52 is a predetermined waveform determined depending on the resistance value of the quenching resistor 54 and the like. In a normal MPPC, the resistance values of the quenching resistors 54 of all the photodetection pixels 52 are set to be the same resistance value. In this case, the N photodetection pixels 52 output detection signals S0 having substantially the same time waveform.

On the other hand, in the photodetector 50 according to the above configuration example, the N photodetection pixels 52 have the specific configuration in which the quenching resistors 54 of the N photodetection pixels 52 have resistance values different from each other. With this configuration, it is possible to appropriately achieve a configuration in which the N photodetection pixels 52 of the photodetector 50 output detection signals S0 having time waveforms different from each other.

Further, regarding the configuration of the N photodetection pixels 52 of the photodetector 50 that output detection signals having time waveforms different from each other, various configurations other than the configuration illustrated in FIG. 1 is applicable.

Figure 4:
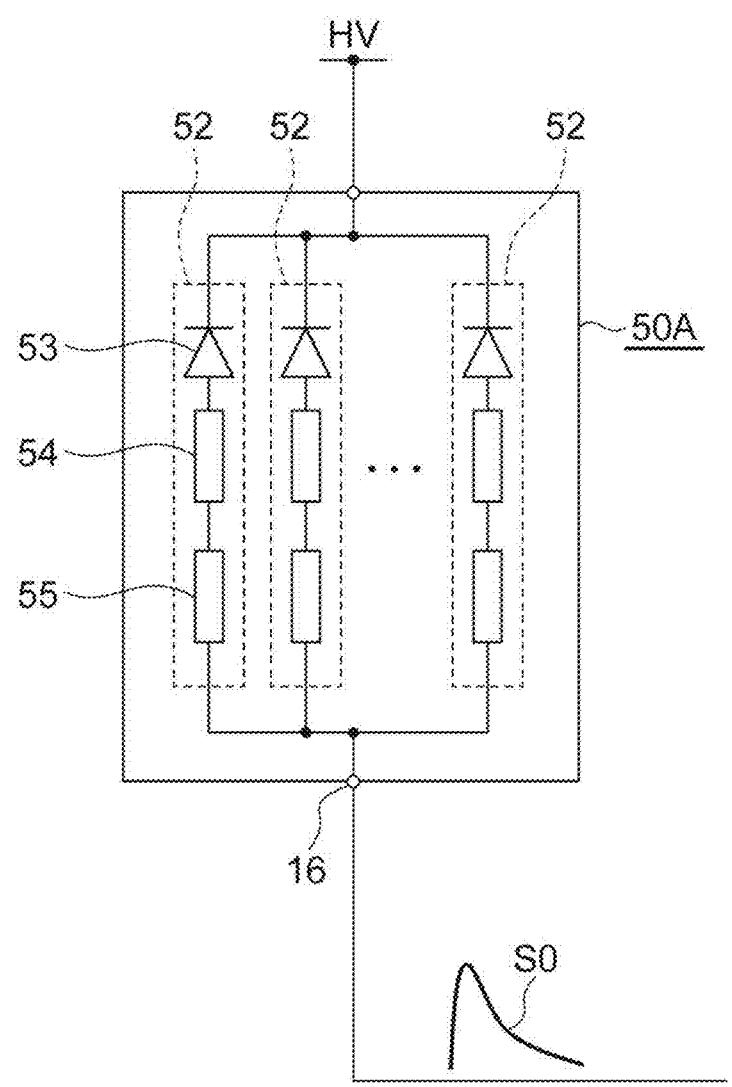
FIG. 4 is a diagram schematically illustrating a configuration of a photodetector of a second embodiment.

FIG. 4 is a diagram schematically illustrating a configuration of a photodetector of a second embodiment. Similarly to the photodetector 50, a photodetector 50A according to the present embodiment includes N photodetection pixels 52 that are arranged one-dimensionally or two-dimensionally and each generate a detection signal S0 in response to incidence of light, and a single output terminal 16 that outputs the detection signal S0 generated in each of the N photodetection pixels 52 to the outside.

Each of the N photodetection pixels 52 of the photodetector 50A includes an APD 53 that operates in Geiger mode, a quenching resistor 54 connected in series to the APD 53, and a frequency filter 55 connected in series between the quenching resistor 54 and the output terminal 16.

Further, in this configuration example, the photodetector 50A is configured such that the frequency filters 55 of the N photodetection pixels 52 have frequency characteristics different from each other. With this configuration, it is also possible to appropriately achieve a configuration in which the N photodetection pixels 52 of the photodetector 50A output detection signals S0 having time waveforms different from each other.

Further, in this configuration, the frequency filters 55 of the N photodetection pixels 52 are, for example, high-pass filters, low-pass filters, or band-pass filters having cutoff frequencies different from each other. Further, in this configuration example, the quenching resistors 54 of the N photodetection pixels 52 may have the same resistance value or may have resistance values different from each other.

Figure 5:
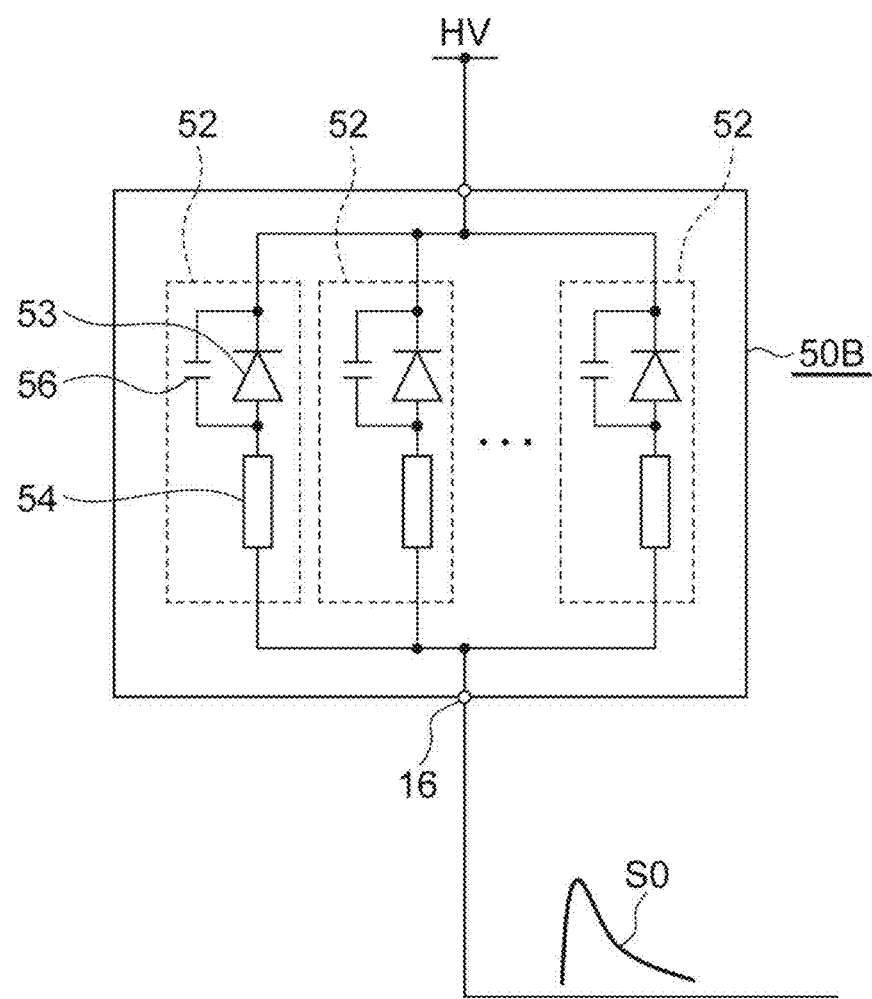
FIG. 5 is a diagram schematically illustrating a configuration of a photodetector of a third embodiment.

FIG. 5 is a diagram schematically illustrating a configuration of a photodetector of a third embodiment. Similarly to the photodetector 50, a photodetector 50B according to the present embodiment includes N photodetection pixels 52 that are arranged one-dimensionally or two-dimensionally and each generate a detection signal S0 in response to incidence of light, and a single output terminal 16 that outputs the detection signal S0 generated in each of the N photodetection pixels 52 to the outside.

Each of the N photodetection pixels 52 of the photodetector 50B includes an APD 53 that operates in Geiger mode, a quenching resistor 54 connected in series to the APD 53, and a capacitor 56 connected in parallel to the APD 53.

Further, in this configuration example, the photodetector 50B is configured such that the capacitors 56 of the N photodetection pixels 52 have capacitance values different from each other. With this configuration, it is also possible to appropriately achieve a configuration in which the N photodetection pixels 52 of the photodetector 50B output detection signals S0 having time waveforms different from each other. Further, in this configuration example, the quenching resistors 54 of the N photodetection pixels 52 may have the same resistance value or may have resistance values different from each other.

Figure 6:
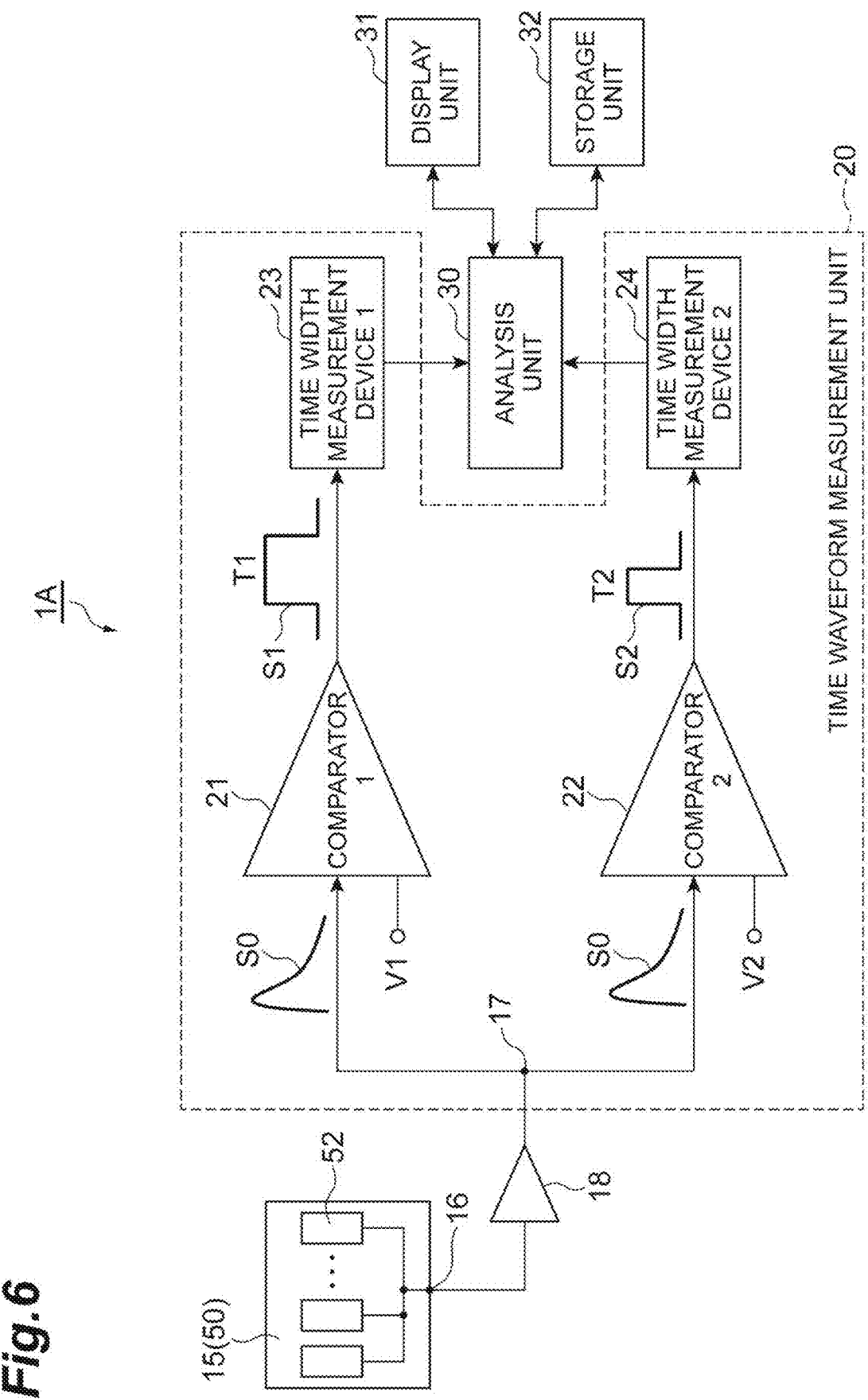
FIG. 6 is a diagram schematically illustrating a configuration of a photodetection device of an embodiment including the photodetector illustrated in FIG. 1.

FIG. 6 is a diagram schematically illustrating a configuration of a photodetection device of an embodiment including the photodetector illustrated in FIG. 1. A photodetection device 1A according to the present embodiment includes a photodetector 15, a time waveform measurement unit 20, and an analysis unit 30. Further, in this configuration example, the photodetector 50 having the configuration illustrated in FIG. 1 is used as the photodetector 15. In addition, as the photodetector 15, the photodetector 50A illustrated in FIG. 4, the photodetector 50B illustrated in FIG. 5, or the like may be used.

The photodetector 15 includes N photodetection pixels 52, detects incident light, and outputs a generated electric signal (voltage signal) as a detection signal S0. The specific configuration of the photodetector 15, the time waveform of the detection signal S0 output from the photodetector 15, and the like are in the above description for the photodetector 50 illustrated in FIG. 1. The detection signal S0 generated by the photodetector 15 is output to the time waveform measurement unit 20 of the subsequent stage via the single output terminal 16 and an amplifier 18. In addition, the amplifier 18 may not be provided if unnecessary.

The time waveform measurement unit 20 is a measurement circuit unit that measures the time waveform of the detection signal S0 output from the output terminal 16 of the photodetector 15. The time waveform measurement unit 20 in the present configuration example includes a first comparator 21, a second comparator 22, a first time width measurement device 23, and a second time width measurement device 24. The detection signal S0 output from the photodetector 15 via the amplifier 18 is branched at a branch point 17, and the branched detection signals S0 are respectively input to the first comparator 21 and the second comparator 22.

To the first comparator 21, a first threshold voltage V1 is applied. The first comparator 21 compares the detection signal S0, which is a voltage signal, with the first threshold voltage V1, and outputs a first digital signal S1 having a first time width T1 corresponding to a time during which the voltage value of the detection signal S0 exceeds the threshold voltage V1. Further, to the second comparator 22, a second threshold voltage V2 having a voltage value different from that of the first threshold voltage V1 is applied. The second comparator 22 compares the detection signal S0 with the second threshold voltage V2, and outputs a second digital signal S2 having a second time width T2 corresponding to a time during which the voltage value of the detection signal S0 exceeds the threshold voltage V2.

The first time width measurement device 23 measures the first time width T1 of the first digital signal S1 output from the first comparator 21, and outputs the obtained data on the first time width T1 to the analysis unit 30 of the subsequent stage. Further, the second time width measurement device 24 measures the second time width T2 of the second digital signal S2 output from the second comparator 22, and outputs the obtained data on the second time width T2 to the analysis unit 30. Each of the first time width measurement device 23 and the second time width measurement device 24 is preferably configured by a time to digital converter (TDC).

The analysis unit (analysis device) 30 obtains, based on the first time width T1 and the second time width T2 respectively input from the first and second time width measurement devices 23 and 24, a time constant $\tau$, which is a parameter indicating the time waveform of the detection signal S0. The time constant $\tau$ is, for example, a fall time $\tau d$ of the time waveform of the detection signal S0 to be described later. Further, the analysis unit 30 may obtain, as the time constant $\tau$, a parameter indicating the time waveform other than the fall time $\tau d$. Further, the analysis unit 30 may further obtain a pulse height E of the time waveform of the detection signal S0 based on the time constant $\tau$ as necessary. As the analysis unit 30, a computer including a CPU and a memory, a field programmable gate array (FPGA), or the like can be used, for example.

A display unit (display device) 31 and a storage unit (storage device) 32 are connected to the analysis unit 30. The display unit 31 displays an analysis result of the detection signal S0 by the analysis unit 30, such as the time constant $\tau$ derived as described above, as necessary. The storage unit 32 stores data on the first and second time widths T1 and T2 input to the analysis unit 30, data on the analysis result, such as the time constant $\tau$ derived by the analysis unit 30, and the like.

The effect of the photodetection device 1A according to the above embodiment is described.

In the photodetection device 1A illustrated in FIG. 6, the photodetector 15 including the N photodetection pixels 52 configured to output detection signals S0 having time waveforms different from each other and the single output terminal 16 that outputs the detection signal S0 is used, and the time waveform measurement unit 20 that measures the time waveform of the detection signal S0 output from the photodetector 15, and the analysis unit 30 are provided. With this configuration, the analysis unit 30 obtains the time constant τ indicating the time waveform of the detection signal S0 in response to detection of light, and it is thereby possible to appropriately acquire information that the detection signal S0 is output from which one of the N photodetection pixels 52.

Further, in the above photodetection device 1A, specifically, the time waveform measurement unit 20 has the configuration in which the first and second comparators 21 and 22 in which the threshold voltages V1 and V2 different from each other are set are provided for the detection signal S0 from the photodetector 15. Then, different time widths of the first and second digital signals S1 and S2 respectively output from the comparators 21 and 22 are measured by the first and second time width measurement devices 23 and 24, and the time constant τ, which is a parameter indicating the time waveform of the detection signal S0, is obtained by the analysis unit 30 based on the obtained first time width T1 and second time width T2. With this configuration, it is possible to appropriately acquire and determine information on the time waveform of the detection signal S0 with a simple configuration without performing waveform sampling or the like.

Further, in the above photodetection device 1A, the analysis unit 30 may determine, based on the time constant τ obtained for the detection signal S0, which one of the N photodetection pixels 52 has output the detection signal S0. With this configuration, it is possible to reliably determine the photodetection pixel 52 based on the time constant τ of the detection signal S0.

Further, in the above photodetection device 1A, the analysis unit 30 may further obtain, based on the time constant τ, the pulse height E of the time waveform of the detection signal S0 in addition to the time constant τ. With this configuration, it is possible to easily obtain the pulse height E of the detection signal S0 at high speed with low power consumption without providing a pulse height measurement device, such as an analog to digital converter (ADC), separately from the time waveform measurement unit 20 including the comparators 21 and 22 and the time width measurement devices 23 and 24. In addition, the pulse height E may not be obtained if unnecessary.

Figure 7:
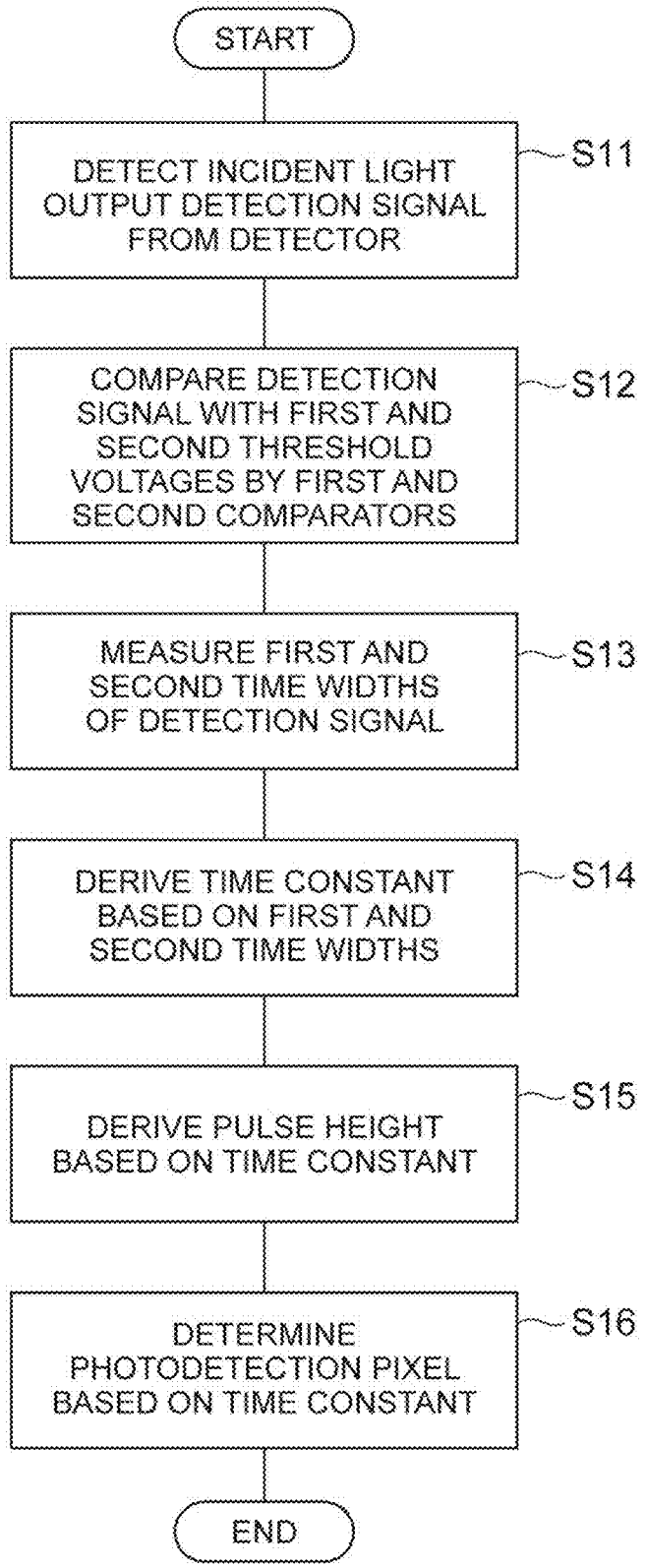
FIG. 7 is a flowchart illustrating a photodetection method in the photodetection device illustrated in FIG. 6.
Figure 8:
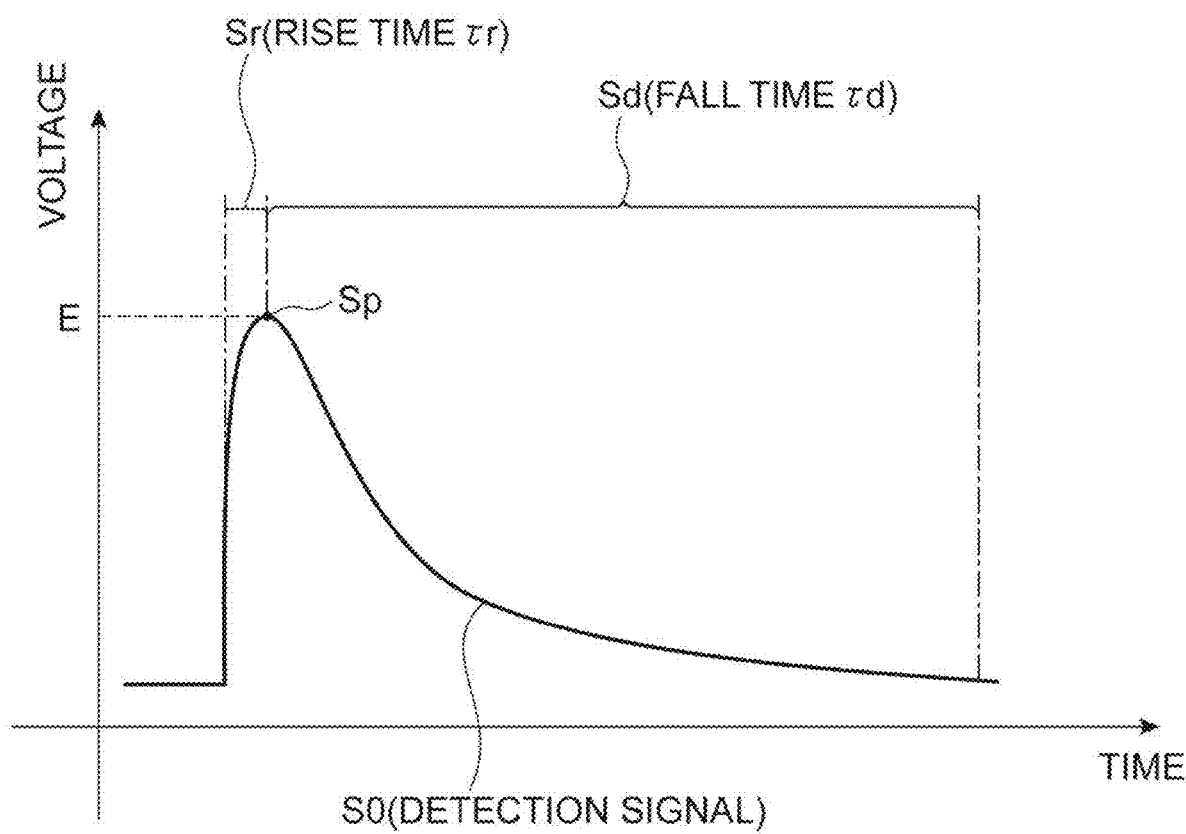
FIG. 8 is a graph illustrating a time waveform of a detection signal output from a photodetector.
Figure 9:
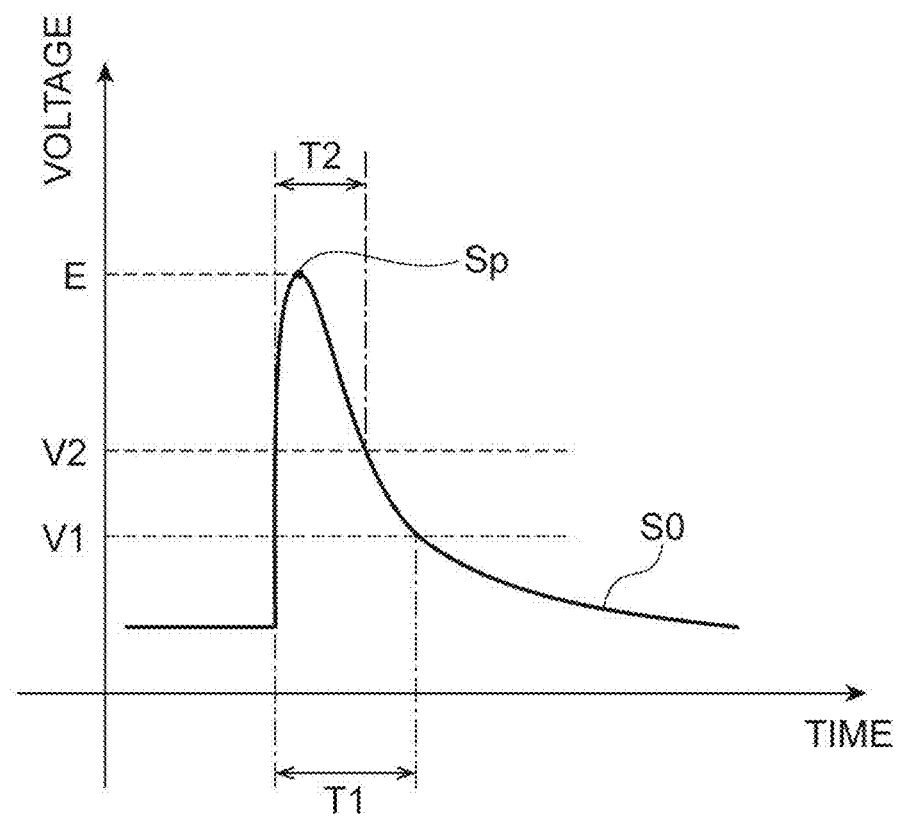
FIG. 9 is a graph illustrating first and second time widths of a detection signal.

FIG. 7 is a flowchart illustrating a photodetection method performed in the photodetection device 1A illustrated in FIG. 6. Further, FIG. 8 is a graph illustrating the time waveform of the detection signal S0 output from the photodetector 15. Further, FIG. 9 is a graph illustrating the first and second time widths T1 and T2 obtained by applying the first and second threshold voltages V1 and V2 to the detection signal S0. In the following, a photodetection method according to the present embodiment will be described together with specific examples of the time waveform of the detection signal S0 and a method of deriving the time constant and the like.

In the photodetection method illustrated in FIG. 7, first, light (for example, a single photon) is detected by the photodetector 15 including the above photodetector 50 or the like, and a detection signal S0 is output from the output terminal 16 of the photodetector 15 in response to the incidence of the light (step S11). FIG. 8 schematically illustrates an example of the time waveform of the detection signal S0 output from the photodetector 15. In the graph of FIG. 8, the horizontal axis indicates time, and the vertical axis indicates the voltage value of the detection signal S0.

In the time waveform of the detection signal S0 illustrated in FIG. 8, the part before a signal peak Sp is a signal rising part Sr, and the part after the signal peak Sp is a signal falling part Sd. Further, the time waveform of the detection signal S0 having a shape illustrated in FIG. 8 can be expressed by, for example, the following Formula (1).

[Formula 1]

$$f(t) = E\left(1 + \frac{\tau_d}{\tau_r}\right)^{\tau_r/\tau_d} \left\{1 - \left(\frac{\tau_d}{\tau_r}\right)^{-1}\right\}^{-1} e^{-\frac{t}{\tau_d}}\left(1 - e^{-\frac{t}{\tau_r}}\right) \quad (1)$$

Here, in Formula (1), E represents a pulse height that is a voltage value at the signal peak Sp, τr represents a rise time (rise time constant) of the signal rising part Sr, and τd represents a fall time (fall time constant) of the signal falling part Sd.

The detection signal S0 output from the photodetector 15 is input to the first and second comparators 21 and 22 in the time waveform measurement unit 20 via the amplifier 18 and the branch point 17. The first comparator 21 compares the detection signal S0 with the first threshold voltage V1 and outputs the first digital signal S1 having the first time width T1 corresponding to a time during which the voltage value of the detection signal S0 exceeds the threshold voltage V1, as illustrated in the graph of FIG. 9. Further, the second comparator 22 compares the detection signal S0 with the second threshold voltage V2 and similarly outputs the second digital signal S2 having the second time width T2 corresponding to a time during which the voltage value of the detection signal S0 exceeds the threshold voltage V2 (step S12). The first and second time widths T1 and T2 are respectively measured by the first and second time width measurement devices 23 and 24 (step S13).

In addition, FIG. 8 and FIG. 9 illustrate that the signal peak Sp of the time waveform of the detection signal S0 is in the positive direction with respect to the voltage, but if the signal peak Sp of the detection signal S0 is in the negative direction with respect to the voltage, the time width is only required to be, for example, a time width corresponding to a time during which the voltage value of the detection signal S0 the positive/negative of which is inverted exceeds the threshold voltage. This corresponds to a time during which the voltage value of the original detection signal is below the threshold voltage.

The analysis unit 30 derives the time constant indicating the time waveform of the detection signal S0 based on the first and second time widths T1 and T2 and the like measured by the first and second time width measurement devices 23 and 24 (step S14). Further, the analysis unit 30 derives the pulse height E of the time waveform of the detection signal S0 based on the first and second time widths T1 and T2, the time constant τ, and the like, as necessary (step S15). Further, the analysis unit 30 determines, based on the obtained time constant τ, which one of the N photodetection pixels (photodetection units) has output the detection signal S0 (step S16).

Here, in the time waveform of the detection signal S0 output from the photodetector 15, if the rise time τr is sufficiently shorter than the fall time τd, the first time width T1 of the detection signal S0 for the first threshold voltage V1 is expressed by the following Formula (2).

[Formula 2]

$$T1 = \tau_d \log \frac{E}{V1} \quad (2)$$

Further, the second time width T2 of the detection signal S0 for the second threshold voltage V2 is similarly expressed by the following Formula (3).

[Formula 3]

$$T2 = \tau_d \log \frac{E}{V2} \quad (3)$$

Thus, when the time constant τ derived by the analysis unit 30 as a parameter of the time waveform is the fall time τd of the time waveform of the detection signal S0, the time constant τ can be obtained with the following Formula (4).

[Formula 4]

$$\tau = \tau_d = (T1-T2)/\log(V2/V1) \quad (4)$$

With Formula (4), it is possible to appropriately easily obtain the time constant τ of the detection signal S0.

Further, when the analysis unit 30 obtains the pulse height E of the detection signal S0 in addition to the time constant τ, the pulse height E can be obtained with the following Formula (5) using the fall time τd obtained as the time constant τ.

[Formula 5]

$$E = V1 \exp \frac{T1}{\tau_d} = V2 \exp \frac{T2}{\tau_d} \quad (5)$$

In addition, the first and second threshold voltages V1 and V2 in the first and second comparators 21 and 22 can be arbitrarily set and adjusted so as to easily obtain the time constant τ and the like.

Further, regarding the above waveform condition that the rise time τr is sufficiently shorter than the fall time τd in the detection signal S0, specifically, it is preferable that, for example, the rise time τr of the time waveform of the detection signal S0 with the fall time τd satisfies the following condition.

$$(\tau r/\tau d) < 0.1$$

In addition, in this configuration example, the photodetector 15 includes the N photodetection pixels 52 as described above, and the number N of the photodetection pixels 52 may be arbitrarily set to two or more. For example, when the photodetector 15 includes a first photodetection pixel that outputs a detection signal having a predetermined time waveform, and a second photodetection pixel that outputs a detection signal having a time waveform different from that of the first photodetection pixel, it is possible to determine, based on the obtained time constant τ, whether the detection signal S0 is output from the first photodetection pixel or the second photodetection pixel.

Figure 10:
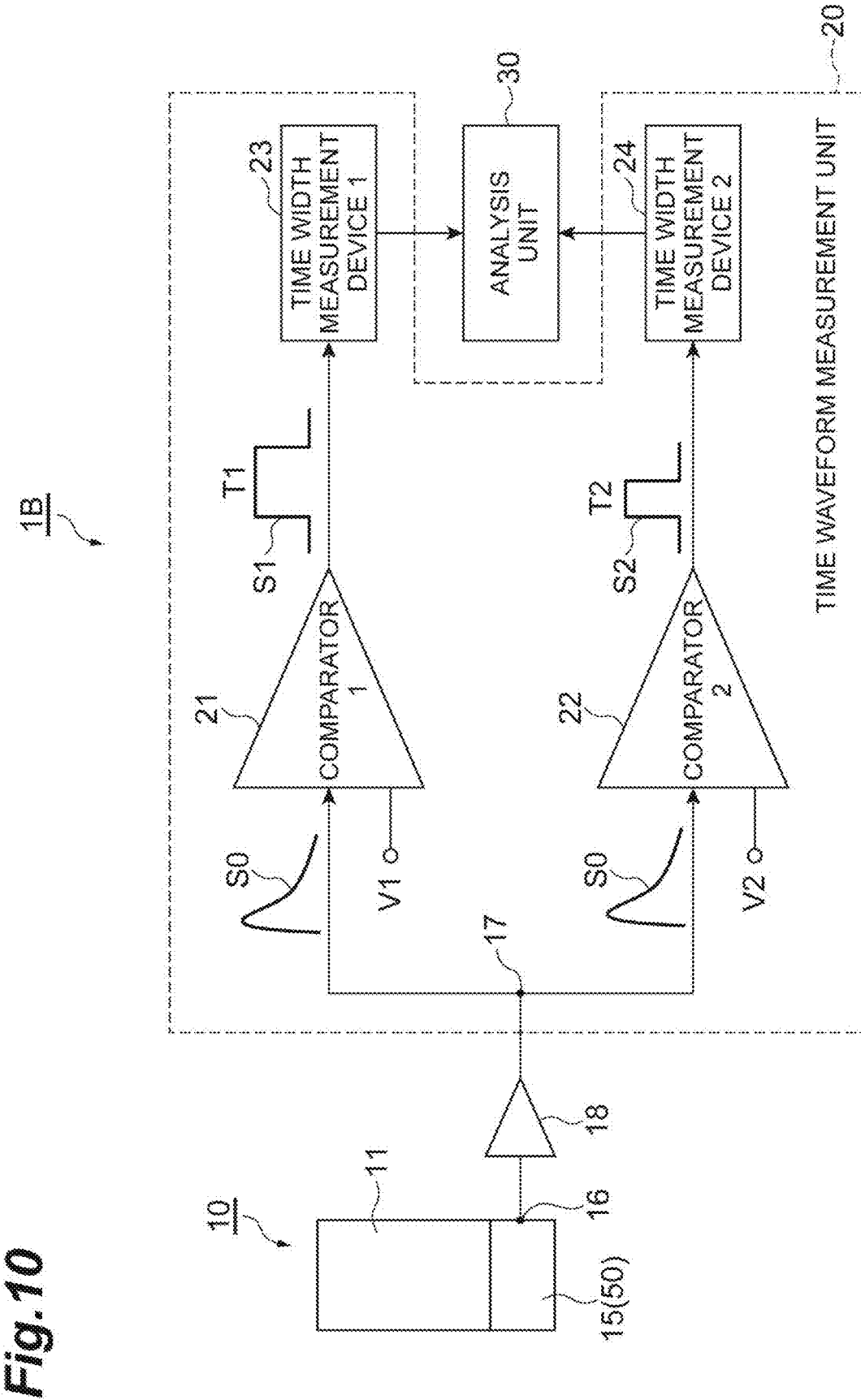
FIG. 10 is a diagram schematically illustrating a configuration of a radiation detection device of an embodiment including the photodetector illustrated in FIG. 1.

The photodetection device 1A illustrated in FIG. 6 can be configured as a radiation detection device by providing a scintillator for the photodetector 15. FIG. 10 is a diagram schematically illustrating a configuration of a radiation detection device of an embodiment including the photodetector illustrated in FIG. 1. A radiation detection device 1B according to the present embodiment includes a radiation detector 10, a time waveform measurement unit 20, and an analysis unit 30. Among these, the configurations of the time waveform measurement unit 20 and the analysis unit 30 are similar to those illustrated in FIG. 6. Further, in FIG. 10, a display unit 31 and a storage unit 32 connected to the analysis unit 30 are not illustrated.

The radiation detector 10 detects an incident radiation ray and outputs a generated electric signal (voltage signal) as a detection signal. The radiation detector 10 in this configuration example includes a scintillator 11 and a photodetector 15. The scintillator 11 is made of a predetermined scintillation material, and generates scintillation light in response to incidence of a radiation ray to be detected. The time waveform of the scintillation light generated in the scintillator 11 is a predetermined waveform determined depending on the light emission characteristics of the scintillation material. Further, the radiation ray to be detected by the scintillator 11 is, for example, a γ ray, an X ray, an electron, a charged particle, a cosmic ray, or the like.

The photodetector 15 detects the scintillation light output from the scintillator 11 and outputs a detection signal. In this configuration example, the photodetector 50 having the configuration illustrated in FIG. 1 is used as the photodetector 15. In addition, as the photodetector 15, the photodetector 50A illustrated in FIG. 4, the photodetector 50B illustrated in FIG. 5, or the like may be used. Further, the time waveform of the detection signal S0 is a predetermined waveform determined depending on the time waveform of the scintillation light described above, the configuration of the photodetection pixels 52 in the photodetector 15, and the like.

Figure 11:
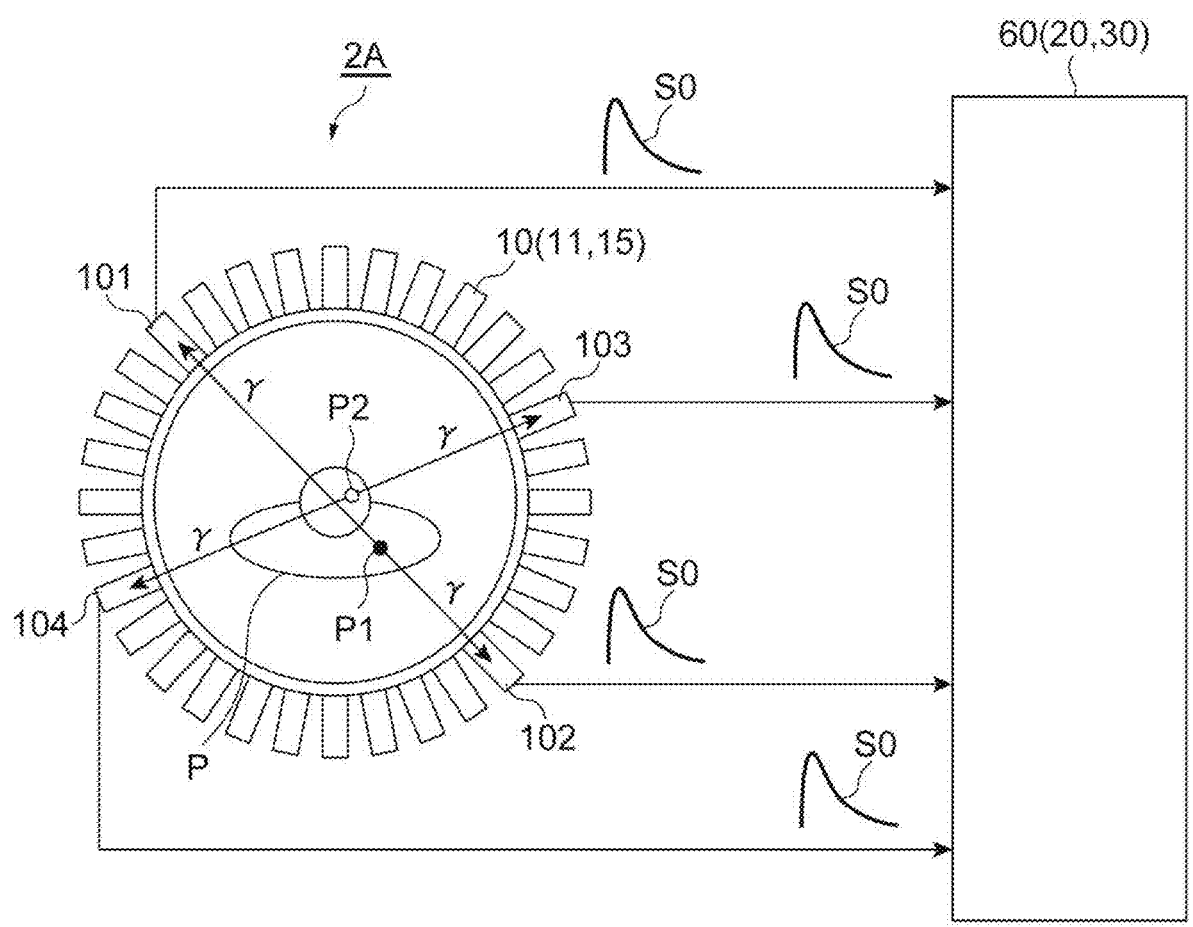
FIG. 11 is a diagram illustrating a configuration of a PET apparatus using the detecting device illustrated in FIG. 10.

The radiation detection device 1B having the configuration illustrated in FIG. 10 can be suitably applied to, for example, a PET apparatus. FIG. 11 is a diagram illustrating a configuration of a PET apparatus to which the radiation detection device illustrated in FIG. 10 is applied. A PET apparatus 2A is configured by arranging a plurality of radiation detectors 10 each including the scintillator 11 and the photodetector 15 so as to surround a subject P. Further, for the detection signal S0 output from each radiation detector 10, a signal processing unit 60 including the time waveform measurement unit 20 and the analysis unit 30 illustrated in FIG. 6 and FIG. 10 is provided.

In the PET apparatus 2A, a pair of γ rays generated by annihilation of the positron inside the subject P is detected by the radiation detectors 10. In the example illustrated in FIG. 11, a pair of γ rays generated at a measurement point P1 inside the subject P is detected by radiation detectors 101 and 102. Further, a pair of γ rays generated at a measurement point P2 is detected by radiation detectors 103 and 104.

The detection signal S0 output from the photodetector 15 of the radiation detector 10 is input to the signal processing unit 60, and the signal processing unit 60 measures the time waveform of the detection signal S0 and derives the time constant τ of the time waveform, as described above with reference to FIG. 6. Further, based on the obtained time constant τ, determination of the photodetection pixel 52 in the photodetector 15 or the like is performed. Information on determination of the photodetection pixel and the like can be used, for example, to improve the performance of the PET apparatus 2A.

Further, FIG. 12 is a table showing rise times τr and fall times τd of time waveforms of scintillation light output from scintillators. FIG. 12 shows rise times τr and fall times τd of time waveforms of existing scintillators of LSO, LYSO, LaRr3, GSO, and GAGG used in PET apparatuses. These scintillators are considered to sufficiently satisfy the waveform condition that the rise time τr is sufficiently shorter than the fall time τd.

The photodetector and the photodetection device according to the present invention are not limited to the above embodiments and configuration examples, and can be variously modified. For example, in the configurations illustrated in FIG. 6 and FIG. 10, the amplifier 18 is provided for the detection signal S0 output from the photodetector 15, however, this amplifier 18 may not be provided if unnecessary. Further, the time waveform measurement unit 20 that measures the time waveform of the detection signal S0 may have various configurations. Further, the analysis unit 30 is only required to obtain the time constant τ of the detection signal S0 based on the measurement result by the time waveform measurement unit 20.

Further, the N photodetection pixels 52 of the photodetector 50 that output detection signals S0 having time waveforms different from each other are not limited to the configurations illustrated in FIG. 1, FIG. 4, and FIG. 5, and may have various configurations.

The photodetector of the above embodiment is configured to include (1) N photodetection pixels (N is an integer of 2 or more) arranged one-dimensionally or two-dimensionally and each for generating a detection signal in response to incidence of light, and (2) a single output terminal for outputting the detection signal generated in each of the N photodetection pixels, and (3) each of the N photodetection pixels includes an avalanche photodiode operating in Geiger mode, and a quenching resistor connected in series to the avalanche photodiode, and (4) the N photodetection pixels are configured to output detection signals having time waveforms different from each other.

Here, in the above photodetector, the N photodetection pixels may have a specific configuration in which the quenching resistors of the N photodetection pixels have resistance values different from each other. With this configuration, it is possible to appropriately achieve a configuration in which the N photodetection pixels output detection signals having time waveforms different from each other.

Further, the N photodetection pixels may have a specific configuration in which each of the N photodetection pixels includes a frequency filter connected in series between the quenching resistor and the output terminal, and the frequency filters of the N photodetection pixels have frequency characteristics different from each other. With this configuration, it is also possible to appropriately achieve a configuration in which the N photodetection pixels output detection signals having time waveforms different from each other.

When the frequency filters are provided in the photodetection pixels as described above, specifically, the frequency filters of the N photodetection pixels may be high-pass filters, low-pass filters, or band-pass filters having cutoff frequencies different from each other.

Further, the N photodetection pixels may have a specific configuration in which each of the N photodetection pixels includes a capacitor connected in parallel to the avalanche photodiode, and the capacitors of the N photodetection pixels have capacitance values different from each other. With this configuration, it is also possible to appropriately achieve a configuration in which the N photodetection pixels output detection signals having time waveforms different from each other.

The photodetection device of the above embodiment is configured to include (1) a photodetector having the above configuration, (2) a time waveform measurement unit for measuring the time waveform of the detection signal output from the output terminal of the photodetector, and (3) an analysis unit for obtaining a time constant indicating the time waveform of the detection signal based on a measurement result by the time waveform measurement unit.

The photodetection device may have a specific configuration in which the time waveform measurement unit includes a first comparator for comparing the detection signal with a first threshold voltage and outputting a first digital signal having a first time width corresponding to a time during which a voltage value of the detection signal exceeds the first threshold voltage, a first time width measurement device for measuring the first time width of the first digital signal, a second comparator for comparing the detection signal with a second threshold voltage different from the first threshold voltage and outputting a second digital signal having a second time width corresponding to a time during which the voltage value of the detection signal exceeds the second threshold voltage, and a second time width measurement device for measuring the second time width of the second digital signal, and the analysis unit obtains the time constant of the detection signal based on the first time width and the second time width.

In the above photodetection device, the first and second comparators in which threshold voltages different from each other are set are provided for the detection signal output from the photodetector. Then, the different time widths of the first and second digital signals output from the two comparators are measured by the first and second time width measurement devices, and the time constant which is a parameter indicating the time waveform of the detection signal in response to the detection of light is obtained based on the obtained first time width and second time width. With this configuration, it is possible to appropriately acquire and determine information on the time waveform of the detection signal with a simple configuration.

Further, in the above photodetection device, the analysis unit may determine, based on the obtained time constant, which one of the N photodetection pixels has output the detection signal. With this configuration, it is possible to reliably determine the photodetection pixel based on the time constant of the detection signal.

INDUSTRIAL APPLICABILITY

The present invention can be used, with a configuration including a plurality of photodetection pixels and a single output terminal, as a photodetector and a photodetection device capable of appropriately identifying and determining a photodetection pixel detecting light.

REFERENCE SIGNS LIST 50, 50A, 50B—photodetector, 51—region, 52—photodetection pixel, 53—avalanche photodiode (APD), 54—quenching resistor, 55—frequency filter, 56—capacitor, 58—common electrode, 59—signal line, 1A—photodetection device, 1B—radiation detection device, 2A—PET apparatus, 10—radiation detector, 11—scintillator, 15—photodetector, 16—output terminal, 17—branch point, 18—amplifier, 20—time waveform measurement unit, 21—first comparator, 22—second comparator, 23—first time width measurement device, 24—second time width measurement device, 30—analysis unit, 31—display unit, 32—storage unit, 60—signal processing unit, S0—detection signal, Sp—signal peak, Sr—signal rising part, Sd—signal falling part, S1—first digital signal, S2—second digital signal, V1—first threshold voltage, V2—second threshold voltage, T1—first time width, T2—second time width.

The invention claimed is:

1. A photodetection device comprising:
 a photodetector;
 a time waveform measurement unit; and
 an analysis unit, wherein
 the photodetector includes:
  N photodetection pixels (N is an integer of 2 or more) arranged one-dimensionally or two-dimensionally and each configured to generate a detection signal in response to incidence of light; and
  a single output terminal configured to output the detection signal generated in each of the N photodetection pixels, wherein
  each of the N photodetection pixels includes an avalanche photodiode operating in Geiger mode, and a quenching resistor connected in series to the avalanche photodiode,
  the N photodetection pixels are configured to output detection signals having time waveforms different from each other,
  the time waveform measurement unit is configured to measure the time waveform of the detection signal output from the output terminal of the photodetector, and
  the analysis unit is configured to obtain a time constant indicating the time waveform of the detection signal based on a measurement result by the time waveform measurement unit, and wherein
 the time waveform measurement unit includes:
  a first comparator configured to compare the detection signal with a first threshold voltage and output a first digital signal having a first time width corresponding to a time during which a voltage value of the detection signal exceeds the first threshold voltage;
  a first time width measurement device configured to measure the first time width of the first digital signal;
  a second comparator configured to compare the detection signal with a second threshold voltage different from the first threshold voltage and output a second digital signal having a second time width corresponding to a time during which the voltage value of the detection signal exceeds the second threshold voltage; and
  a second time width measurement device configured to measure the second time width of the second digital signal, and wherein
  the analysis unit is configured to obtain the time constant of the detection signal based on the first time width and the second time width.

2. The photodetection device according to claim 1, wherein the quenching resistors of the N photodetection pixels have resistance values different from each other.

3. The photodetection device according to claim 1, wherein each of the N photodetection pixels includes a frequency filter connected in series between the quenching resistor and the output terminal, and
 the frequency filters of the N photodetection pixels have frequency characteristics different from each other.

4. The photodetection device according to claim 3, wherein the frequency filters of the N photodetection pixels are high-pass filters, low-pass filters, or band-pass filters having cutoff frequencies different from each other.

5. The photodetection device according to claim 1, wherein each of the N photodetection pixels includes a capacitor connected in parallel to the avalanche photodiode, and
 the capacitors of the N photodetection pixels have capacitance values different from each other.

6. The photodetection device according to claim 1, wherein the analysis unit is configured to determine, based on the time constant, which one of the N photodetection pixels has output the detection signal.

* * * * *